United States Patent [19]

Naé et al.

[11] Patent Number: 5,429,999

[45] Date of Patent: * Jul. 4, 1995

[54] ORGANOCLAY COMPOSITIONS CONTAINING TWO OR MORE CATIONS AND ONE OR MORE ORGANIC ANIONS, THEIR PREPARATION AND USE IN NON-AQUEOUS SYSTEMS

[75] Inventors: Hemi N. Naé, Princeton Junction; William W. Reichert, Freehold; Alice C. Eng, Princeton Jct. all of N.J.

[73] Assignee: Rheox, Inc., Hightstown, N.J.

[*] Notice: The portion of the term of this patent subsequent to Aug. 9, 2011 has been disclaimed.

[21] Appl. No.: 241,443

[22] Filed: May 11, 1994

Related U.S. Application Data

[63] Continuation-in-part of Ser. No. 791,318, Nov. 14, 1991, Pat. No. 5,336,647.

[51] Int. Cl.⁶ ............................................. C04B 33/02
[52] U.S. Cl. ................................. 501/146; 501/148; 106/487; 252/8.7; 252/8.8; 252/315.2; 210/723
[58] Field of Search ............ 252/8.7, 8.8, 315.2; 501/146, 148; 106/486, 487; 210/660, 723

[56] References Cited

U.S. PATENT DOCUMENTS

| | | | |
|---|---|---|---|
| 4,287,086 | 9/1981 | Finlayson et al. | 252/316 |
| 4,444,665 | 4/1984 | Hildebrandt | 210/660 |
| 4,742,098 | 5/1988 | Finlayson et al. | 252/315.2 |
| 5,075,033 | 12/1991 | Cody et al. | 252/315.2 |
| 5,110,501 | 5/1992 | Knudson, Jr. et al. | 252/315.2 |
| 5,336,647 | 8/1994 | Nae et al. | 501/146 |

*Primary Examiner*—Mark L. Bell
*Assistant Examiner*—Michael Marcheschi
*Attorney, Agent, or Firm*—Michael J. Cronin

[57] ABSTRACT

A novel organophilic clay gellant comprising the reaction product of:

(a) a smectite clay having a cation exchange capacity of at least 75 milliequivalents per 100 grams of natural clay without impurities;

(b) a first organic cation in an amount of from about 75% to about 150% of the cation exchange capacity of the smectite clay;

(c) a second organic cation provided by a polyalkoxylated quaternary ammonium salt; and (d) one or more organic anion(s) that is capable of reacting with said first and second organic cations, to form an organic cation-organic anion complex with said smectite clay.

The organophilic clay gellant is used in a non-aqueous fluid system such as paints, inks, and coatings to provide improved theological properties.

18 Claims, No Drawings

ORGANOCLAY COMPOSITIONS CONTAINING TWO OR MORE CATIONS AND ONE OR MORE ORGANIC ANIONS, THEIR PREPARATION AND USE IN NON-AQUEOUS SYSTEMS

RELATED APPLICATION

This application is a continuation in part of U.S. patent application Ser. No. 07/791318 filed Nov. 14, 1991 now U.S. Pat. No. 5,336,647 by the instant inventors.

BACKGROUND OF THE INVENTION

1. Brief Description of the Field of the Invention

The present invention relates to novel organophilic clays which are dispersible in non-aqueous fluids to provide rheological properties to such fluids. The invention also pertains to a process for preparing these organophilic clays using multiple cations such as quaternary ammonium compounds, and one or more organic anions. The invention includes non-aqueous fluid compositions including such organophilic clays as rheological additives.

2. Description of the Prior Art

It has long been known that organophilic clays can be used to thicken a variety of organic compositions. Such organophilic clays are prepared by the reaction of an organic cation with a clay in various methods known in the art. If the organic cation contains at least one alkyl group containing at least 8 to 10 carbon atoms, then such organoclays have the property of increasing viscosity in organic liquids and thus providing rheological properties to a wide variety of such liquids including paints, coatings, adhesives and similar products.

It is also well known that such organoclays may function to thicken polar or non-polar solvents, depending on the substituents on the organic salt. J. W. Jordan, in "Proceedings of the 10th National Conference on Clays and Clay Minerals" (1963), discusses a wide range of applications of organoclays from high polarity liquids to low polarity liquids.

The efficiency of organophilic clays in non-aqueous systems can be further improved by adding a low molecular weight polar organic material to the composition. Such polar organic materials have been called dispersants, dispersion aids, solvating agents and the like. See, for example, U.S. Pat. Nos. 2,677,661; 2,704,276; 2,833,720; 2,879,229; and 3,294,683. The most efficient polar materials for use as such have been found to be low molecular weight alcohols and ketones, particularly methanol and acetone.

Furthermore, U.S. Pat. Nos. 3,977,894; 4,382,868; 4,464,274; and 4,664,820 describe the preparation of preactivated organophilic clay gellants that are used to thicken organic compositions wherein the activators are admixed with the organophilic clay.

More recently, organophilic clay gellants have been developed which are the reaction products of smectite-type clays having a cation exchange capacity with certain organic cations or organic cations and organic anion combinations. These gellants have the advantage of being effectively dispersible in particular organic compositions without the need for a dispersion aid under normal shear conditions. Illustrative patents which describe such improved organophilic clay gellants are U.S. Patent Nos. 4,105,578; 4,208,218; 4,287,086; 4,391,637, 4,410,364; 4,412,018; 4,434,075; 4,434,076; 4,450,095; and 4,517,112.

One way to enhance the gelling and dispersing efficiency of an organophilic clay is to replace some of the hydrophobic side groups attached to the organic cation with hydroxyalkyl groups. In these groups, the hydroxyl group is attached to any carbon atom on an aliphatic radical, except for the carbon atom adjacent to the positively charged atom as disclosed in U.S. Pat. No. 4,434,076.

To further impart improved gelling properties, the groups attached to the organic salt may be replaced by a mono- or polyhydroxylated group. Modified organophilic clays containing these compounds swell and gel in organic liquids without the need for polar dispersion additives. For example, European Patent Application 0,133,071 describes modified organophilic clays resulting from the combination of a smectite clay, a quaternary ammonium salt having a long hydrocarbon chain, and a mono- or polyhydroxylated nitrogeneous surfactant. The mono- and polyhydroxylated nitrogeneous organic surfactants used in the disclosed formulations are ethoxylated amines and alkoxylated quaternary ammonium salts having long hydrocarbon chains, such as (tallow alkyl)- or di(tallow alkyl)-(methyl or benzyl) ammonium salts.

Further increases in the amount of alkoxylated groups, however, result in clay compositions that impart gelling properties to aqueous systems rather than to non-aqueous systems. For example, U.S. Pat. No. 4,677,158 describes a reaction product of a smectite clay and a quaternary ammonium compound that is used as a thickener for aqueous suspensions, particularly water based latex paints and caulks. The disclosed quaternary ammonium compound is said to consist of a nitrogen atom bonded to separate carbon chains where one chain can be a methyl group or alkyl group containing 10 to 20 carbon atoms, and the second chain is an alkyl group containing from 10 to 22 carbon atoms or a polyoxyethylene chain, The third and fourth chains are polyoxyethylene chains such that the total number of ethylene oxide units is from 5 to 200 moles, The disadvantages of most existing organoclay compositions for non-aqueous systems are that (a) relatively large amounts of the organoclay compositions are needed to impart the required viscosity; (b) polar activators are required in many cases to enhance their gelling properties; and (c) the organoclays are limited to either polar or non-polar systems depending upon their organic content.

SUMMARY OF THE INVENTION

A new type of organophilic clay gellant has been discovered in which the synergistic action of two or more types of organic cations derived from organic salt compounds in addition to the presence of an organic anion provides improved gelling properties in organic solvents, the first organic cation employed in the formulations of the invention contains hydrophobic groups whereas the second organic cation contains hydrophilic groups, It has been unexpectedly discovered that the combination of these hydrophobic and hydrophilic organic salts and the organic anion provides an organophilic clay gellant which exhibits improved gelling properties in non-aqueous systems, The present invention provides an improved, more efficient organophilic clay gellant for gelling or thickening non-aqueous solvent-based compositions.

Thus, according to one aspect of the invention, an organophilic clay gellant is provided which comprises the reaction product of:

(a) a smectite-type clay having a cation exchange capacity of at least 75 milliequivalents per 100 grams of clay;

(b) a first organic cation in an amount of from about 75% to about 150% of the cation exchange capacity of the smectite-type clay;

(c) a second organic cation provided by a polyalkoxylated quaternary ammonium salt from about 0.01% to 20% by weight of the total organic cation content; and (d) one or more organic anion(s) that is capable of reacting with the first and the second organic cations to form a complex.

The present invention also contemplates a process for preparing an organophilic clay gellant which comprises:

(a) preparing an aqueous slurry of a smectite-type clay having a cation exchange capacity of at least 75 milliequivalents per 100 grams of clay;

(b) heating the slurry to a temperature between about 20° C. and 100° C.;

(c) adding to the slurry:
(i) a first organic cation in an amount of from about 75% to about 150% of the cation exchange capacity of the smectite-type clay;
(ii) a second organic cation provided by a polyalkoxylated quaternary ammonium salt from about 0.01% to 20% by weight of the total organic cation content; and
(iii) one or more organic anion(s) that is capable of reacting with the first and/or second organic cations;

(d) reacting the resulting mixture for a sufficient time to form an organophilic clay gellant; and (e) recovering the organophilic clay gellant.

The first and second organic cations and the organic anion may be added to the clay slurry separately in any order or simultaneously.

The invention also provides non-aqueous solvent compositions thickened with the above-indicated organophilic clay gellant. A third aspect of the invention therefore relates to a non-aqueous fluid system which comprises:

(a) a non-aqueous composition; and (b) an organophilic clay gellant comprising the reaction product of:
(i) a smectite-type clay having a cation exchange capacity of at least 75 milliequivalents per 100 grams of clay;
(ii) a first organic cation in an amount of from about 75% to about 150% of the cation exchange capacity of the smectite-type clay;
(iii) a second organic cation provided by a polyalkoxylated quaternary ammonium salt from about 0.01% to 20% by weight of the total organic cation content; and
(iv) one or more organic anions that is capable of reacting with the first and the second organic cations to form a complex.

DESCRIPTION OF THE PREFERRED EMBODIMENTS

As stated above, one aspect of the present invention relates to an improved, more efficient organophilic clay gellant. The organophilic clay is prepared by reacting a smectite-type clay with a first hydrophobic organic cation, a second hydrophilic organic cation provided by a polyalkoxylated quaternary ammonium salt, and an organic anion.

According to a first aspect of the invention, an organophilic clay gellant is provided which comprises the reaction product of:

(a) a smectite-type clay having a cation exchange capacity of at least 75 milliequivalents per 100 grams of clay;

(b) a first organic cation in an amount of from about 75% to about 150% of the cation exchange capacity of the smectite-type clay;

(c) a second organic cation provided by a polyalkoxylated quaternary ammonium salt from about 0.01% to 20% by weight of the total organic cation content; and (d) one or more organic anion(s) that is capable of reacting with the first and the second organic cations to form a complex.

The clay which is used in the present invention is a smectite-type clay having a cationic exchange capacity of at least 75 milliequivalents per 100 grams of clay as determined by the well-known ammonium acetate method.

Smectite-type clays are well known in the art and are commercially available from a variety of sources. Prior to use in the formulations of the instant invention, the clays are preferably converted to the sodium form if they are not already in this form. This may be conveniently carried out by preparing an aqueous clay slurry and passing the slurry through a bed of cation exchange resin in the sodium form. Alternatively, the clay can be mixed with water and a soluble sodium compound, such as sodium carbonate, sodium hydroxide, etc., and the mixture sheared, such as with a pugmill or extruder. Conversion of the clay to the sodium form can be undertaken at any point before reaction with the reagents of the invention.

Smectite-type clays prepared synthetically by either a pneumatolytic or, preferably, a hydrothermal synthesis process may also be used to prepare the novel organic clay complexes of the invention.

Representative of smectite-type clays useful in accordance with the present invention are the following:

Montmorillonite

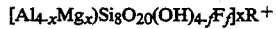
$[Al_{4-x}Mg_x)Si_8O_{20}(OH)_{4-f}F_f]xR^+$ where $0.55 \leq x \leq 1.10$, $f \leq 4$ and R is selected from the group consisting of Na, Li, NH$_4$, and mixtures thereof;

Bentonite

$[Al_{4-x}Mg_x(Si_{8-y}Al_y)O_{20}(OH)_{4-f}F_f](x+y)R^+$ where $0 < x < 1.10$, $0 < y < 1.10$, $0.55 \leq (x+y) < 1.10$, $f < 4$ and R is selected from the group consisting of Na, Li, NH$_4$ and mixtures thereof;

Beidellire

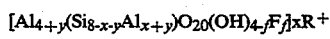
$[Al_{4+y}(Si_{8-x-y}Al_{x+y})O_{20}(OH)_{4-f}F_f]xR^+$ where $0.55 \leq x \leq 1.10$, $0 \leq y \leq 0.44$, $f \leq 4$ and R is selected from the group consisting of Na, Li, NH$_4$ and mixtures thereof;

Hectorite

$[Mg_{6-x}Li_xSi_8O_{20}(OH)_{4-f}F_f](x+y)xR^+$ where $0.57 \leq x \leq 1.15$, $f \leq 4$ and R is selected from the group consisting of Na, Li, NH$_4$, and mixtures thereof;

Saponite

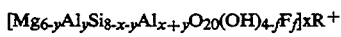
$$[Mg_{6-y}Al_ySi_{8-x-y}Al_{x+y}O_{20}(OH)_{4-f}F_f]xR^+$$

where $0.58 \leq x \leq 1.18$, $0 \leq y \leq 0.66$, $f \leq 4$ and R is selected from the group consisting of Na, Li, NH$_4$, and mixtures thereof; and Stevensite

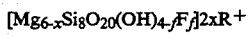
$$[Mg_{6-x}Si_8O_{20}(OH)_{4-f}F_f]2xR^+$$

where $0.28 \leq x \leq 0.57$, $f=4$ and R is selected from the group consisting of Na, Li, NH$_4$, and mixtures thereof.

The preferred clays used in the present invention are bentonite and hectorite. In addition, it will be understood that the above listed smectite-type clays which have been subjected to the application of shear may also be used.

To achieve shearing of the smectite-type clay, the clay is typically dispersed in water at a concentration of from about 0.5 to about 80% by weight. The slurry may optionally be first centrifuged to remove non-clay impurities which constitute about 10% to about 50% of the starting clay composition. Of course, if the clay has previously been treated, such as by the clay vendor, to remove the impurities, the treated clay can be formed into a slurry and subjected to shear conditions. Shear can be imparted to the smectite-type clay slurry by means of commercially available equipment that is known to impart high shear to the material. Illustrative of such equipment are a Manton-Gaul in Homogenizer available form Manton-Gaul in Company, a Tekmar SD-45 Homogenizer available from Tekmar Company, a Sharples Super Centrifuge available from Sharples Division of Pennwalt Corporation, an Oakes mill available from Oakes Machinery, a Waring Blendor available from Waring Products, a Microfluidizer available from Microfluidics Corporation, a division of Biotechnology Corporation, and similar devices which can impart high laminar and turbulent shear to the clay slurry. Exemplary conditions using a Manton-Gaul in homogenizer are a pressure in the range from about 500 to about 8,000 psi with one or more passes of the clay slurry through the homogenizer. Representative processes for shearing clay slurries are described in U.S. Patents No. 4,695,402 and 4,743,098, both of which are herein incorporated by reference.

The smectite-type clays may be synthesized hydrothermally by forming an aqueous reaction mixture in the form of a slurry containing mixed hydrous oxides or hydroxides of the desired metals with or without, sodium (or alternate exchangeable cation or mixture thereof) fluoride in the proportions defined by the above formulas and the preselected values of x, y and f for the particular synthetic smectite desired. The slurry is then placed in an autoclave and heated under autogenous pressure to a temperature within the range of approximately 100° to 325° C., preferably 275° to 300° C., for a sufficient period of time to form the desired product. Formulation times of 3 to 48 hours are typical at 300° C. depending upon the particular smectite-type clay being synthesized. The optimum time can be readily determined by pilot trials.

Representative hydrothermal processes for preparing synthetic smectite clays are described in U.S. Pat. Nos. 3,252,757; 3,586,478; 3,666,407; 3,671,190; 3,844,978; 3,844,979; 3,852,405 and 3,855,147, all of which are herein incorporated by reference.

The cationic organic salts which are useful in this invention may be selected from a variety of materials that are capable of forming an organoclay by exchange of cations with the smectite-type clay. The organic cations which are reacted with the smectite-type clay must have a positive charge localized on a single atom or on a small group of atoms within the compound. For example, the cation may be provided by a compound selected from the group consisting of quaternary ammonium salts, phosphonium salts, sulfonium salts and mixtures thereof. The first organic cation is preferably a cation which contains at least one linear or branched, saturated or unsaturated alkyl groups having 12 to 22 carbon atoms. The remaining groups of the cation may be selected from the group consisting of (a) linear or branched aliphatic, alicyclic or aromatic groups having 1 to 22 carbon atoms; (b) aralkyl groups which are benzyl and substituted benzyl moieties including fused ring moieties having linear or branches 1 to 22 carbon atoms in the alkyl portion of the structure; (c) aryl groups such as phenyl and substituted phenyl including fused ring aromatic substituents; (d) beta, gamma-unsaturated groups having six or less carbon atoms or hydroxyalkyl groups having 2 to 6 carbon atoms; and (e) hydrogen.

The long chain alkyl radicals may be derived from naturally occurring oils including various vegetable oils, such as corn oil, coconut oil, soybean oil, cottonseed oil, castor oil and the like, as well as various animal oils or fats such as tallow oil. The alkyl radicals may likewise be petrochemically derived from, for example, alpha olefins.

Representative examples of useful branched, saturated radical s include 12-methyl stearyl and 12-ethyl stearyl. Representative examples of useful branched, unsaturated radical s include 12-methyloleyl and 12-ethyloleyl. Representative examples of unbranched saturated radicals include lauryl; stearyl; tridecyl; myristyl (tetradecyl); pentadecyl; hexadecyl; hydrogenated tallow, docosanyl. Representative examples of unbranched, unsaturated and unsubstituted radicals include oleyl, linoleyl, linolenyl, soya and tallow.

Additional examples of aralkyl, that is benzyl and substituted benzyl moieties, include those materials derived from, e.g., benzyl halides, benzhydryl halides, trityl halides, alpha-halo-alpha-phenylalkanes wherein the alkyl chain has from 1 to 22 carbon atoms, such as 1-halo-1-phenylethane, 1-halo-1-phenypropane, and 1-halo-1-phenyloctadecane; substituted benzyl moieties, such as those derived from ortho-, meta- para-chlorobenzyl halides, para-methoxy- benzyl halides, ortho-, meta- and para-nitrilobenzyl halides, and ortho-, meta- and para-alkylbenzyl halides wherein the alkyl chain contains from 1 to 22 carbon atoms; and fused ring benzyl-type moieties, such as those derived from 2-halomethylnaphthalene, 9-halomethylanthracene and 9-halomethylphenathrene, wherein the halo group comprises chloro, bromo, iodo, or any other such group which serves as a leaving group in the nucleophilic attack of the benzyl type moiety such that the nucleophile replaces the leaving group on the benzyl type moiety.

Examples of aryl groups that are useful in the first organic cation include phenyl and substituted phenyl, N-alkyl and N,N-dialkyl anilines, wherein the alkyl groups contain between 1 and 22 carbon atoms; ortho-, meta- and para-nitrophenyl, ortho-, meta- and para-alkyl phenyl, wherein the alkyl group contains between 1 and 22 carbon atoms, 2-, 3-, and 4-halophenyl wherein the halo group is defined as chloro, bromo, or iodo, and 2-, 3-, and 4-carboxyphenyl and esters thereof, where the alcohol of the ester is derived from an alkyl alcohol, wherein the alkyl group contains between 1 and 22 carbon atoms, aryl such as a phenol, or aralkyl such as benzyl alcohols; fused ring aryl moieties such as naphthalene, anthracene, and phenanthrene.

The beta, gamma unsaturated alkyl group which may be included in the first organic cation component of the organophilic clay gellants of the invention may be selected from a wide range of materials well known in the art. These compounds may be cyclic or acyclic, unsubstituted or substituted with aliphatic radicals containing up to 3 carbon atoms such that the total number of aliphatic carbons on the beta, gamma unsaturated radical is 6 or less. The beta, gamma unsaturated alkyl radical may be substituted with an aromatic ring that likewise is conjugated with the unsaturation of the beta, gamma moiety or the beta, gamma radical may be substituted with both aliphatic radicals and aromatic rings.

Representative examples of cyclic beta, gamma unsaturated alkyl groups include 2-cyclohexenyl and 2-cyclopentenyl. Representative examples of acyclic beta, gamma unsaturated alkyl groups containing 6 or less carbon atoms include propargyl; allyl(2-propenyl); crotyl(2-butenyl); 2-pentenyl; 2-hexenyl; 3-methyl-2- butenyl; 3-methyl -2-pentenyl; 2,3-dimethyl-2-butenyl; 1,1-dimethyl -2-propenyl; 1,2-dimethyl propenyl; 2,4-pentadienyl; and 2,4-hexadienyl. Representative examples of acyclic-aromatic substituted compounds include cinnamyl(3-phenyl-2 propenyl): 2-phenyl-2-propenyl; and 3-(4-methoxyphenyl)-2-propenyl. Representative examples of aromatic and aliphatic substituted materials include 3-phenyl-2-cyclohexenyl; 3-phenyl-2-cyclopentenyl; 1,1-dimethyl-3-phenylpropenyl; 1,1,2-trimethyl -3-phenyl-2-propenyl; 2,3-dimethyl-3-phenyl-2-propenyl; 3,3-dimethyl - 2-phenyl-2propenyl; and 3-phenyl-2-butenyl.

The hydroxyalkyl group may be selected from a hydroxyl substituted aliphatic radical wherein the hydroxyl is not substituted at the carbon atom adjacent to the positively charged atom; the group has from 2 to 6 aliphatic carbon atoms. The alkyl group may be substituted with an aromatic ring independently from the 2 to 6 aliphatic carbons. Representative examples include 2-hydroxyethyl; 3-hydroxypropyl; 4-hydroxypentyl; 6-hydroxyhexyl; 2-hydroxypropyl; 2-hydroxybutyl; 2-hydroxypentyl; 2-hydroxyhexyl; 2-hydroxycyclohexyl; 3-hydroxycyclohexyl; 4-hydroxycyclohexyl; 2-hydroxycyclopentyl; 3-hydroxycyclopentyl; 2-methyl -2-hydroxypropyl; 1,1,2-trimethyl-2-hydroxypropyl; 2-phenyl -2-hydroxyethyl; 3-methyl-2-hydroxybutyl; and 5-hydroxy-2pentenyl.

The first organic cation can therefore be provided by a compound selected from the group consisting of at least one of the following formulae:

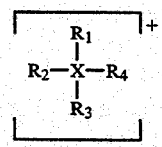

or

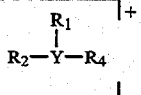

wherein X is nitrogen or phosphorous, Y is sulfur, $R_1$ is a linear or branched, saturated or unsaturated alkyl group having 12 to 22 carbon atoms and $R_2$, $R_3$ and $R_4$ are independently selected from the group consisting of (a) linear or branched alkyl groups having 1 to 22 carbon atoms; (b) aralkyl groups which are benzyl and substituted benzyl moieties including fused ring moieties having linear chains or branches of 1 to 22 carbon atoms in the alkyl portion of the structure; (c) aryl groups such as phenyl and substituted phenyl including fused ring aromatic substituents; (d) beta, gamma unsaturated groups having six or less carbon atoms or hydroxyalkyl groups having 2 to 6 carbon atoms; and (e) hydrogen.

The anion which will normally accompany the organic cation is typically one that will not adversely affect the reaction product or the recovery of the same. Such anions include, for example, chloride, bromide, iodide, hydroxyl, nitrite and acetate, used in amounts sufficient to neutralize the organic cation.

The preparation of the organic salt can be achieved by techniques well-known in the art. For example, when preparing a quaternary ammonium salt, one skilled in the art may prepare a dialkyl secondary amine, for example, by the hydrogenation of nitriles, see U.S. Pat. No. 2,355,356, and then form the methyl dialkyl tertiary amine by reductive alkylations using formaldehyde as a source of the methyl radical. According to procedures set forth in U.S. Pat. Nos. 3,136,819 and 2,775,617, a quaternary amine halide may then be formed by adding benzyl chloride or benzyl bromide to the tertiary amine. The disclosure of the above three patents are incorporated herein by reference.

As is well known in the art, the reaction of the tertiary amine with benzyl chloride or benzyl bromide may be completed by adding a minor amount of methylene chloride to the reaction mixture so that a blend of products which are predominantly benzyl substituted is obtained. This blend may then be used without further separation of components to prepare the organophilic clay. Illustrative of the numerous patents which describe organic cationic salts, their manner of preparation and their use in the preparation of organophilic clays are commonly assigned U.S. Pat. Nos. 2,966,506; 4,081,496; 4,105,578; 4,116,866; 4,208,218; 4,391,637; 4,410,364; 4,412,018; 4,434,075; 4,434,076; 4,450,095 and 4,517,112; the contents of which are incorporated herein by reference.

The instant invention is based on the unexpected discovery that the combination of hydrophobic and hydrophilic organic cations and one or more organic anion(s) provides a synergistic effect in which the organoclay complex containing the organic salts imparts improved viscosity to non-aqueous systems containing the organoclay complex. [he organophilic clay gellant provided by the invention imparts a higher viscosity to non-aqueous systems (at a given concentration) than is achieved by separately adding an organophilic clay gellant containing only the first organic cation and organic anion(s) of the invention and a second organophilic clay gellant containing only the second organic cation of the invention and mixtures thereof.

The second organic cation utilized in the products of the invention comprises a quaternary ammonium salt which contains alkoxy moieties. The second organic cation contains at least one linear or branched alkoxylated group containing at least two carbon atoms and one oxygen atom.

The compound is preferably a hydrophilic agent having the following general formula:

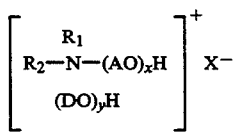

wherein $R_1$, $R_2$ are independently selected from the group consisting of (a) linear or branched alkyl groups having 1 to 22 carbon atoms; (b) aralkyl groups which are benzyl and substituted benzyl moieties including fused ring moieties having linear chains or branches of 1 to 22 carbon atoms in the alkyl portion of the structure; (c) aryl groups such as phenyl and substituted phenyl including fused ring aromatic substituents; (d) beta, gamma unsaturated groups having six or less carbon atoms; and (e) hydroxyalkyl groups having 2 to 6 carbon atoms; x and y represent the number of repeating alkyl oxide groups and are integers and the total $x+y$ may be 1 to 200. The alkyl oxide (AO, DO) groups may include independently, two to eight carbon atoms such as ethyl, propyl, butyl, pentyl, etc.

The salt anion may be selected from the group consisting of halogen anions, preferably chloride and bromide, hydroxide, acetate, nitrite, and the like and mixtures thereof. These anions are required to have such charge that they neutralize the alkoxylated quaternary ammonium salt.

Illustrative examples of suitable alkoxylated quaternary ammonium chloride compounds include those available under the tradename Ethoquad from Akzo Chemie America, namely, methyl bis(2-hydroxyethyl)-cocoalkyl ammonium chloride, methyl bis(polyoxyethylene (15)) cocoalkyl quaternary ammonium chloride, methyl bis(2-hydroxyethyl) oleyl ammonium chloride, methyl bis(polyoxyethylene (15)) oleyl quaternary ammonium chloride, methyl bis(2-hydroxyethyl) octadecyl ammonium chloride, and methyl bis(polyoxyethylene (15)) octadecyl quaternary ammonium chloride.

The organic anion(s) employed in the products of the invention may be selected from a wide range of materials that are capable of reacting with the first and second organic cations in order to form an organic cation/organic anion complex. The molecular weight of the organic anion is preferably 3,000 or less, and more preferably 1,000 or less, and contains at least one anionic moiety per molecule so as to permit the formation of the organic cation/organic anion complex.

Preferred organic anions are derived from carboxylic acids, such as stearic acid, oleic acid, palmitic acid, succinic acid, tartaric acid, etc.; sulfonic acids; and alkyl sulfates, such as the lauryl half ester of sulfuric acid.

The organic anion, which may include mixtures of organic anions, is reacted with the organic cations and smectite-type clay to form the desired organophilic clay gellant. The organic anion may be added to the reaction mixture in acid or salt form. Exemplary of the latter form are alkali metal salts, alkaline earth salts, ammonium and organic amines.

Representative salts of the organic anion are those formed with hydrogen, lithium, sodium, potassium, magnesium, calcium, barium, ammonium and organic amines such as ethanolamine, diethanolamine, triethanolamine, methyldiethanolamine, butyldiethanolaine, diethylamine, dimethylamine, triethylamine, dibutylamine, and so forth, and mixtures thereof. The most preferred salt form is with sodium.

The amount of organic anion reacted with the smectite-type clay and the organic cations must be sufficient to obtain a milliequivalent ratio of organic cations to organic anion in the range of from about 1.70:1.0 to about 50:1.0, preferably from about 3.0:1.0 to about 15:1.0. The most preferred ranges depend on the particular organic cations and organic anion utilized and the intended environment of use and can be determined by experimentation guided by the information set forth above. Illustrative patents which describe suitable organic anions that may be co-reacted with the organic cations and the smectite-type clay in order to form the organophilic clay include commonly assigned U.S. Pat. Nos. 4,412,018; 4,434,075, and 4,517,112.

The present invention also contemplates a process for preparing an organophilic clay gellant which comprises:

(a) preparing an aqueous slurry of a smectite-type clay having a cation exchange capacity of at least 75 milliequivalents per 100 grams of clay;

(b) heating said slurry to a temperature between about 20° C. and 100° C.;

(c) adding to said slurry:

(i) a first organic cation in an amount of from about 75% to about 150% of the cation exchange capacity of the smectite-type clay;

(ii) a second organic cation provided by a polyalkoxylated quaternary ammonium salt in an amount from about 0.01% to 20% by weight of the total organic cation content; and (iii) one or more organic anion(s) that is capable of reacting with the first and the second organic cations to form a complex.

(d) reacting the resulting mixture for a sufficient time to form an organophilic clay gellant; and (e) recovering said organophilic clay gellant.

The organoclays of this invention may be prepared by admixing the clay, organic salts and water together, preferably at temperatures within the range from 20° C. to 100° C., and most preferably from 35° C. to 80° C. for a period of time sufficient for the organic compounds to react with the clay. The reaction is followed by filtering, washing, drying and grinding. The organic salts may be added simultaneously or at separate intervals in any order.

The clay is preferably dispersed in water at a concentration from about 1 to 80%, most preferably, from 2 to 8%. Optionally, the slurry may be centrifuged to remove non-clay impurities which may constitute about 10% to 50% of the starting clay composition.

The amount of organic salts added to the clay for purposes of this invention must be sufficient to impart to the clay the improved gelling and dispersion characteristics. This amount is defined as the milliequivalent ratio, which is the amount of milliequivalents (m.e.) of the organic salt in the organoclay per 100 grams of natural clay, without impurities. The organic salts of this invention must have a combined milliequivalent ratio of 1 to 150, preferably 75 to 125 m.e. The amount of the hydrophobic organic cation should be from about 1 to 149.99 m.e., preferably from 75 to 149.99. The amount of the hydrophilic organic cation employed should be from about 0.01 to about 30 m.e., preferably from 1 to 15 m.e. The organic anion may be present in amounts of from about 1 to 66 milliequivalents, preferably from about 6 to about 35 milliequivalents of anion for example, oleate, palmitate, tartrate, succinate, stearate and the like and mixtures thereof.

The organophilic clay gellants prepared according to the this invention may be used as rheological additives in non-aqueous compositions such as paints, varnishes, enamels, waxes, paint-varnish lacquer remover, oil base drilling fluids, lubricating grease, inks, polyester resins, epoxy resins, mastices, adhesives, sealants, cosmetics, detergents, and the like. These fluids are prepared by any conventional method as described in U.S. Pat. No. 4,208,218, including colloid mills, roller mills, ball mills and high speed dispersers. Consequently, the invention also provides non-aqueous solvent compositions thickened with the above-indicated organophilic cay gellant. Thus, a third aspect of the invention relates to a non-aqueous fluid system which comprises:

(a) a non-aqueous composition; and
(b) an organophilic clay gellant comprising the reaction product of:
  (i) a smectite-type clay having a cation exchange capacity of at least 75 milliequivalents per 100 grams of cay;
  (ii) a first organic cation in an amount of from about 75% to about 150% of the cation exchange capacity of the smectite-type clay;
  (iii) a second organic cation provided by a polyalkoxylated quaternary ammonium salt in an amount of 0.01% to about 20% by weight of the total organic cation content; and
  (iv) one or more organic anion(s) that is capable of reacting with the first and/or the second organic cations to form a complex.

The organophilic clay complexes of the invention are added to the non-aqueous compositions in amounts sufficient to obtain the desired rheological properties. Amounts of the organophilic clay complexes in the non-aqueous compositions are from about 0.01% to 15%, preferably from about 0.3% to 5%, based on the total weight of the non-aqueous fluid system.

The following examples are given to illustrate the invention, but are not deemed to be limiting thereof. All percentages given throughout the specification are based upon weight unless otherwise indicated. It should be noted that Organic Salts A and B referred to in the following examples provide the first and second organic cations, respectively, of these inventive formulations.

EXAMPLE 1

This example illustrates the preparation of an organophilic clay gellant according to the present invention.

45.00 grams of dried bentonite clay, which has been previously treated in water by centrifugation to remove non-clay impurities and ion-exchanged to provide the clay in sodium form, is mixed with water to form a 3% by weight slurry of clay in water. The slurry is heated to 70° C. in a reaction flask of suitable size equipped with a stirrer, thermometer and addition funnel. 2.08 grams of methyl bis(polyoxyethylene (15)) cocoalkyl quaternary ammonium chloride (5 milliequivalents per 100 grams of clay solids) dissolved in 10 grams of isopropyl alcohol is added to the clay slurry. The mixture is stirred at 70° C. for 1 hour. 27.20 grams of dimethyl dihydrogenated tallow quaternary ammonium chloride (107 milliequivalents per 100 grams of clay solids) dissolved in 100 grams of isopropanol at about 60° C. is added to the mixture. 2.88 grams of palmitic acid is then added to the reaction flask. The mixture is stirred for another hour at 70° C. The product is filtered through a Buchner funnel to collect the solids. The wet solids are reslurried in 1500 grams of water at 70° C. for 20 minutes and then re-collected on a Buchner funnel. The filtercake is dried in a 60° C. oven for 16 hours.

Comparative Example A

For comparative purposes, the procedure of Example 1 is repeated, except that the hydrophilic quaternary ammonium chloride and the organic anion component of the gellant are omitted.

EXAMPLE 2

This Example illustrates the preparation of an organophilic clay gellant according to the invention, wherein the first and second organic cations and the organic anion are added simultaneously to the smectite-type clay slurry.

45.00 grams of dried bentonite clay, which has been previously treated in water by centrifugation to remove non-clay impurities and ion-exchanged to provide the clay in sodium form, is mixed with water to make a 3% by weight slurry of clay in water. The slurry is heated to 70° C. in a reaction flask of suitable size equipped with a stirrer, thermometer and addition funnel. 2.08 grams of methyl bis(polyoxyethylene (15)) cocoalkyl quaternary ammonium chloride (5 meq/100 grams), 27.20 grams of commercially available dimethyl dihydrogenated tallow quaternary ammonium chloride (107 meq/100 grams) and 2.88 grams of palmitic acid are dissolved in 110 grams of isopropyl alcohol at 60° C. and added to the reaction flask. The reaction mixture is stirred for one hour at 70° C. and then filtered through a Buchner funnel to collect the solids. The wet solids are reslurried in 1500 grams on a Buchner funnel. The filtercake is dried at 60° C. in an oven for 16 hours.

EXAMPLE 3

This Example illustrates the preparation of an organophilic clay gellant according to the invention using a sheared smectite-type clay.

About 2.5 gallons of a 3.0% solids slurry of bentonite clay in water, which has been previously treated by centrifugation to remove non-clay impurities and ion-exchanged to provide the clay in the sodium form, is passed through a Manton-Gaul in homogenizer at 5,000 psi pressure. 1500 grams of this slurry is placed in a reaction vessel of suitable size equipped with a stirrer, thermometer, and addition funnel. The clay slurry is heated to 70° C. 2.08 grams of methyl bis(polyoxyethylene (15)) cocoalkyl quaternary ammonium chloride (5 meq/100 grams) dissolved in 10 grams of isopropyl alcohol is added to the clay slurry. The mixture is stirred at 70° C. for one hour. 27.20 grams of dimethyl dihydrogenated tallow quaternary ammonium chloride (107 meq/100 grams) which has been dissolved in 100 grams of isopropyl alcohol at about 60° C. is added to the mixture. 2.88 grams of palmitic acid is then added to the reaction flask. The reaction mixture is stirred for one additional hour at 70° C. and then filtered through a Buchner funnel to collect the solids. The wet solids are reslurried in 1500 grams of water at 70° C. for 20 minutes and then recollected on a Buchner funnel. The filtercake is dried at 60° C. in an oven for 16 hours.

EXAMPLES 4–12

The compositions are prepared according to the procedure set forth in Example 1 (or Example 3 for sheared clay) except that different amounts of the methyl bis(-polyoxyethylene (15)) cocoalkyl quaternary ammonium chloride (commercially available form Akzo Chemie as Ethoquad C/25) (Organic Salt B) and commercially available dimethyl dihydrogenated tallow quaternary ammonium chloride (Organic Salt A) are used as shown in Table 1. The amount of palmitic acid is maintained constant in the formulations of Examples 4–12.

TABLE 1

| Example | Organic Salt A* meg/100 grams** | Organic Salt B meg/100 grams** | Organic Anion* meg/100 grams** | Clay |
|---|---|---|---|---|
| 4 | 111 | 1 | 25 | Bentonite |
| 1 | 107 | 5 | 25 | Bentonite |
| 5 | 102 | 10 | 25 | Bentonite |
| 6 | 87 | 25 | 25 | Bentonite |
| 7 | 62 | 50 | 25 | Bentonite |
| 8 | 111 | 1 | 25 | Bentonite (sheared) |
| 9 | 107 | 5 | 25 | Bentonite (sheared) |
| 10 | 102 | 10 | 25 | Bentonite (sheared) |
| 11 | 87 | 25 | 25 | Bentonite (sheared) |
| 12 | 62 | 50 | 25 | Bentonite (sheared) |

*Organic Salt A is dimethyl dihydrogenated tallow quaternary ammonium chloride. Organic Salt B is methyl bis(polyoxyethylene (15)) cocoalkyl quaternary amonium chloride (Ethoquad C/25). The organic anion is palmitate.
**meq/100 grams is milliequivalents per 100 grams of clay solids.

EXAMPLES 13–22

The compositions are prepared according to the procedure set forth in Example 1 (or Example 3 for sheared clay) except that methyl bis(polyoxyethylene (15)) oleyl quaternary ammonium chloride (commercially available from Akzo Chemie as Ethoquad O/25) (Organic Salt B) is substituted for methyl bis(polyoxyethylene (15)) cocoalkyl quaternary ammonium chloride. The amounts of methyl bis(polyoxyethylene (15)) quaternary ammonium chloride, dimethyl dihydrogenated tallow quaternary ammonium chloride and palmitate anion are used as shown in Table 2.

TABLE 2

| Example | Organic Salt A* meg/100 grams** | Organic Salt B meg/100 grams** | Organic Anion* meg/100 grams** | Clay |
|---|---|---|---|---|
| 13 | 111 | 1 | 25 | Bentonite |
| 14 | 107 | 5 | 25 | Bentonite |
| 15 | 102 | 10 | 25 | Bentonite |
| 16 | 87 | 25 | 25 | Bentonite |
| 17 | 62 | 50 | 25 | Bentonite |
| 18 | 111 | 1 | 25 | Bentonite (sheared) |
| 19 | 107 | 5 | 25 | Bentonite (sheared) |
| 20 | 102 | 10 | 25 | Bentonite (sheared) |
| 21 | 87 | 25 | 25 | Bentonite (sheared) |
| 22 | 62 | 50 | 25 | Bentonite (sheared) |

*Organic Salt A is dimethyl dihydrogenated tallow quaternary ammonium chloride. Organic Salt B is methyl bis(polyoxyethylene (15)) oleyl quaternary amonium chloride (Ethoquad O/25). The organic anion is palmitate.
**meq/100 grams is milliequivalents per 100 grams of clay solids.

EXAMPLES 23–26

The preparative procedure set forth in Example 1 is followed except for the substitution of various types and amounts of organic salts as indicated in Table 3.

TABLE 3

| Example | Organic Salt A* meq/100 grams | Organic Salt B* meq/100 grams | Organic Anion* meq/100 grams | Clay |
|---|---|---|---|---|
| 23 | 107 | 5 | 25 | Bentonite |
| 24 | 107 | 5 | 25 | Bentonite |
| 25 | 107 | 5 | 25 | Bentonite |
| 26 | 107 | 5 | 25 | Bentonite |

*Organic Salt A is dimethyl dihydrogenated tallow quaternary ammonium chloride. Organic Salt B is: Ex. 23 - methyl bis(2-hydroxyethyl) oleyl ammonium chloride (Ethoquad O/12); Ex. 24 - methyl bis(2-hydroxyethyl) octadecyl aninonium chloride (Ethoquad 18/12); Ex. 25 - methyl bis(2-hydroxyethyl) cocoalkyl ammonium chloride (Ethoquad C/12); Ex. 26 - methyl bis-(polyoxy ethylene (15)) octadecyl quaternary ammonium chloride (Ethoquad 18/25). The organic anion source is palmitic acid.

EXAMPLES 27–35

These examples illustrate the formation of organophilic clay gellants according to the invention using various organic anions. The preparative procedure set forth in Example I is followed. The types and amounts of organic salts and organic anion sources are indicated in Table 4.

TABLE 4

| Example | Organic Salt A* meq/100 grams | Organic Salt B* meq/100 grams | Organic Anion* |
|---|---|---|---|
| 27 | 107 | 5 | Tartaric acid |

TABLE 4-continued

| Example | Organic Salt A* meq/100 grams | Organic Salt B* meq/100 grams | Organic Anion* |
|---|---|---|---|
| 28 | 107 | 5 | Stearic acid |
| 29 | 107 | 5 | Succinic acid |
| 30 | 107 | 5 | Oleic Acid |
| 31 | 107 | 5 | Sodium Tartrate |
| 32 | 107 | 5 | Disodium tartrate |
| 33 | 107 | 5 | Sodium stearate |
| 34 | 107 | 5 | Disodium succinate |
| 35 | 107 | 5 | Sodium palmitate |

*Organic Salt A is dimethyl dihydrogenated tallow quaternary ammonium chloride. Organic Salt B is methyl bis(polyoxyethylene (15)) cocoalkyl quaternary ammonium chloride (commercially available from Akzo Chemie under the tradename Ethoquad C/25). Organic anion is 25 meq/100 grams. The clay is bentonite.

TABLE 6

| Example | Organic Salt A* meq/100 grams | Organic Salt B* meq/100 grams | Organic Anion* |
|---|---|---|---|
| 45 | 107 | 5(a) | Tartaric acid |
| 46 | 107 | 5(a) | Succinic acid |
| 47 | 107 | 5(a) | Palmitic acid |
| 48 | 107 | 5(a) | Oleic acid |
| 49 | 107 | 5(b) | Tartaric acid |
| 50 | 107 | 5(b) | Succinic acid |
| 51 | 107 | 5(b) | Palmitic acid |
| 52 | 107 | 5(b) | Oleic acid |

*Organic Salt A is dimethyl dihydrogenated tallow quaternary ammonium chloride. Organic Salt B is: (a) - methyl bis(polyoxyethylene (15)) oleyl quaternary ammonium chloride; (b) - methyl bis(2-hydroxyethyl) oleyl ammonium chloride. Organic anion is 25 meq/100 grams. The clay is sheared bentonite.

EXAMPLES 36-44

The preparative procedure set forth in Example 3 is used. The types and amounts of organic salts and organic anion sources are indicated in Table 5.

TABLE 5

| Example | Organic Salt A* meq/100 grams | Organic Salt B* meq/100 grams | Organic Anion* |
|---|---|---|---|
| 36 | 107 | 5 | Tartaric acid |
| 37 | 107 | 5 | Stearic acid |
| 38 | 107 | 5 | Succinic acid |
| 39 | 107 | 5 | Oleic Acid |
| 40 | 107 | 5 | Sodium Tartrate |
| 41 | 107 | 5 | Disodium tartrate |
| 42 | 107 | 5 | Sodium stearate |
| 43 | 107 | 5 | Disodium succinate |
| 44 | 107 | 5 | Sodium palmitate |

*Organic Salt A is dimethyl dihydrogenated tallow quaternary ammonium chloride. Organic Salt B is methyl bis(polyoxyethylene (15)) cocoalkyl quaternary ammonium chloride (comercially available from Akzo Chemie under the tradename Ethoquad C/25). Organic anion is 25 meq/100 grams. The clay is sheared bentonite.

EXAMPLES 45-52

The preparative procedure set forth in Example 3 is used. The types and amounts of organic salts and organic anion sources are indicated in Table 6.

EXAMPLES 53-62

These examples demonstrate the dispersion and viscosity-build properties provided when the organic modified clay complexes of the invention are used in a mineral oil ink formulation. A mineral oil based news red ink is prepared according to Formulation 1.

| | Formulation I News Red Ink Formula | | |
|---|---|---|---|
| Ingredient | Generic Name | Manufacturer | Fomulation (parts by wt.) |
| Part I: Base Red | | | |
| Multi-mix Red Flush 45MM2247 | Red Flush Color | BASF | 26.0 |
| Sunprint HP 750 Mineral Oil | Naphthenic Mineral Oil SUS 750 Viscosity | Sun Refining | 35.0 |
| Nevchem 140 in EXX-Print 705 | Hydrocarbon Resin Solution, 52% Solids | Neville Chemical | 29.0 |
| | | | 90.0 |
| Mix the base at 6000 rpm for 2-3 minutes or until uniform, then add: | | | |
| Part II: Rheological Additive | | | |
| Rheological Additive | | | 3.0 |
| Water | | | 0.2 |
| Disperse the rheological additive in the base at 6000 rpm for 15 minutes, then add: | | | |
| Part III: Letdown | | | |
| EXX-Print | Naphthenic Solvent | Exxon | 7.0 |
| | | Total | 100.2 |

A red ink is prepared according to Formulation 1. The ink is allowed to equilibrate at room temperature for 24 hours. Tack and misting are measured with a Thwing-Albert Inkometer operating at 1200 rpm and 90° F. Tack is measured according to ASTM Method D 4361-84 entitled "Apparent Tack of Printing Inks by the Inkometer.

NPIRI (National Printing Ink Research Institute) grind values are measured to evaluate dispersion according to ASTM Method D 1316-68 entitled "Fineness of grind of Printing Inks by the Production Grindometer." Dispersion ratings are presented in Table 7. The ink is rated for overall scratches and background haze. A dispersion rating of medium heavy indicates poor dispersion resulting in many scratches and a medium to heavy background haze. A rating of light indicates better dispersion properties although some background haze is evident.

Viscosity for the ink formulations are determined using a Brookfield RVT viscometer with a No 15 spindle. Dispersion measurements, Brookfield viscosities, tack, and misting are presented in Table 7.

TABLE 7

| Example | Prep. Ex. | Organic Anion | G-3 Grind | Tack | Misting | Brookfield Viscosity (cP) | |
|---|---|---|---|---|---|---|---|
| | | | | | | 2.5 rpm | 20 rpm |
| 53 | 27 | Tartaric acid | 0/17 M | 4.8 | F | 17000 | 6500 |
| 54 | 30 | Sodium tartrate | 0/10 LM | 4.7 | F | 24000 | 8250 |
| 55 | 31 | Disodium tartrate | 0/20 MH | 4.7 | F | 23000 | 9000 |
| 56 | 28 | Stearic acid | 0/8 LM-M | 4.7 | F | 17000 | 6000 |
| 57 | 32 | Sodium stearate | 0/18 MH | 4.5 | F | 18000 | 7125 |
| 58 | 29 | Succinic acid | 0/13 LM | 5.1 | F | 19000 | 6500 |
| 59 | 33 | Disodium succinate | 0/14 MH | 4.4 | F | 19000 | 7250 |
| 60 | 1 | Palmitic acid | 0/8 LM | 4.7 | F | 15000 | 4500 |
| 61 | 35 | Sodium palmitate | 0/22 MH | 4.4 | F | 7000 | 4000 |
| 62 | Comp. A | None | 0/20 MH | 5.5 | F-P | 4000 | 3250 | where F = Fair; P = Poor; M = Medium; H = Heavy; L = Light.

EXAMPLES 63–65

These Examples demonstrate the dispersion and viscosity-build properties provided when the organic-modified clay complexes are used in a mineral oil ink formulation described in Formulation 1. This set of Examples compares organic-modified clay complexes prepared with sheared bentonite clay to organic-modified clay complexes prepared with non-sheared bentonite clay.

Dispersion measurements, Brookfield viscosities, tack and misting are presented in Table 8.

EXAMPLES 66–78

These Examples demonstrate the dispersion and viscosity-build properties provided when the organic-modified clay complexes are used in a soya bean oil based ink formulation. A red soya news ink formulation is prepared according to Formulation 2.

Formulation 2
Soya News Red Ink Formula

| Ingredient | Generic Name | Manufacturer | Formulation (parts by wt.) |
|---|---|---|---|
| LR 6247 SB Lithol Rubine | Flushed Color | Magruder Color | 26.4 |
| Special T Blown Soya Oil | Oxidized Soya Bean Oil $Z_2$-$Z_4$ | Spencer-Kellogg Div. Reichhold Chemicals | 40.5 |
| Mix at 8000 rpm until uniform, then add: | | | |
| Rheological Additive | | | 3.8 |
| Disperse at 8000 rpm for 20 minutes, then add as letdown: | | | |
| Superior Soya Oil | Highly Refined Soybean Oil A | Spencer-Kellogg Div. Reichhold Chemicals | 29.1 |
| | | Total | 99.8 |

NPIRI (National Printing Ink Research Institute grind values are measured to evaluate dispersion. G-3 grind (dispersion) ratings are presented in Table 9.

Viscosity data for the ink formulations are determined using a Brookfield RVT Viscometer with a No. 15 spindle. Dispersion measurements, Brookfield viscosities, tack, and misting are presented in Table 9.

TABLE 8

| Ex. | Prep. Ex. | Organic Anion | Clay | G-3 Grind | Tack | Misting | Brookfield Viscosity (cP) | |
|---|---|---|---|---|---|---|---|---|
| | | | | | | | 2.5 rpm | 20 rpm |
| 53 | 27 | Tartaric acid | non-sheared | 0/17 M | 4.8 | F | 17000 | 6500 |
| 63 | 36 | Tartaric acid | sheared | 0/22 M | 5.0 | F | 27000 | 8250 |
| 58 | 29 | Succinic acid | non-sheared | 0/13 LM | 5.1 | F | 19000 | 6500 |
| 64 | 38 | Succinic acid | sheared | 0/19 M | 5.1 | F | 26000 | 8125 |
| 60 | 1 | Palmitic acid | non-sheared | 0/8 LM | 4.7 | F | 15000 | 4500 |
| 65 | 3 | Palmitic acid | sheared | 0/22 M | 4.9 | F | 24000 | 6875 |

Where F = Fair; M = Medium = L = Light.

TABLE 9

| Example | Prep. Ex. | Organic Salt B* | Organic Anion | Grind | Tack | Misting | Brookfield Viscosity (cP) | |
|---|---|---|---|---|---|---|---|---|
| | | | | | | | 20 RPM | 2.5 RPM |
| 66 | 36 | a | Tartaric acid | 0/19 MH | 5.5 | F | 3250 | 4000 |
| 67 | 38 | a | Succinic acid | 0/18 M | 5.5 | F | 3750 | 6000 |
| 68 | 3 | a | Palmitic acid | 0/11 LM | 5.3 | F | 4700 | 8000 |
| 69 | 39 | a | Oleic acid | 0/30 MH | 5.5 | F | 3000 | 4000 |
| 70 | 45 | b | Tartaric acid | 0/28 H | 5.3 | F | 4500 | 7000 |
| 71 | 46 | b | Succinic acid | 0/22 MH | 5.2 | F | 4500 | 7000 |
| 72 | 47 | b | Palmitic acid | 0/22 MH | 5.2 | F | 4500 | 9000 |
| 73 | 48 | b | Oleic acid | 0/18 MH | 5.1 | F | 3875 | 7000 |
| 74 | 49 | c | Tartaric acid | 0/15 MH | 5.8 | F | 3625 | 5000 |

TABLE 9-continued

| Example | Prep. Ex. | Organic Salt B* | Organic Anion | Grind | Tack | Misting | Brookfield Viscosity (cP) 20 RPM | Brookfield Viscosity (cP) 2.5 RPM |
|---|---|---|---|---|---|---|---|---|
| 75 | 50 | c | Succinic acid | 0/12 LMM | 5.4 | F | 5250 | 10000 |
| 76 | 51 | c | Palmitic acid | 0/13 MH | 5.2 | F | 3875 | 6000 |
| 77 | 52 | c | Oleic acid | 0/16 MH | 5.2 | F | 3625 | 6000 |
| 78 | Comp. A | — | None | 0/22 MH | 5.7 | F | 3187 | 4000 | where F = Fair; M = Medium; H = Heavy; L = Light.
*Organic Salt B is that of the preparation example, namely:
a — methyl bis(polyoxyethylene (15)) cocoalkyl quaternary ammonium chloride (Ethoquad C/25);
b — methyl bis(polyoxyethylene (15)) oleyl quaternary ammonium chloride (Ethoquad O/25);
c — methyl bis(2-hydroxyethyl) oleyl quaternary ammonium chloride (Ethoquad O/12).
Organic Salt A for each of these examples is dimethyl dihydrogenated tallow quaternary ammonium chloride.

EXAMPLES 79–91

The ink formulations described in Table g were passed through a three roll mill and their properties are presented in Table 10:

TABLE 10

| Example | Ink Ex. | Organic Salt B* | Organic Anion | Brookfield Viscosity (cP) 20 rpm | Brookfield Viscosity (cP) 2.5 rpm |
|---|---|---|---|---|---|
| 79 | 66 | a | Tartaric acid | 10375 | 36000 |
| 80 | 67 | a | Succinic acid | 9875 | 30000 |
| 81 | 68 | a | Palmitic acid | 8250 | 24000 |
| 82 | 69 | a | Oleic acid | 7500 | 29000 |
| 83 | 70 | b | Tartaric acid | 7750 | 21000 |
| 84 | 71 | b | Succinic acid | 10000 | 36000 |
| 85 | 72 | b | Palmitic acid | 7125 | 21000 |
| 86 | 73 | b | Oleic acid | 11250 | 40000 |
| 87 | 74 | c | Tartaric acid | 9125 | 30000 |
| 88 | 75 | c | Succinic acid | 11625 | 44000 |
| 89 | 76 | c | Palmitic acid | 9000 | 32000 |
| 90 | 77 | c | Oleic acid | 9125 | 30000 |
| 91 | 78 | — | None | 6750 | 18000 |

*Organic Salt B is that of the preparation example, namely:
a — methyl bis(polyoxyethylene (15)) cocoalkyl quaternary ammonium chloride (Ethoquad C/25);
b — methyl bis(polyoxyethylene (15)) oleyl quaternary amonium chloride (Ethoquad O/25);
c — methyl bis(2-hydroxyethyl) oleyl quaternary ammonium chloride (Ethoquad O/12).

Based on the foregoing results, it is apparent that the organophilic clay gellants provided by the invention are highly effective in improving the rheological properties of non-aqueous systems. Without wishing to be bound by any particular theory, it is believed that the action of the polyalkoxylated quaternary ammonium cation is required in order to impart the desired hydrophobic/hydrophilic balance to the non-aqueous system, while the organic anion is essential in separating the clay platelets so that they form smaller aggregates with higher surface area. In this regard, reaction products containing the anion appear to be more "open" in structure than those containing no anion. It is believed that these compositions expose more surface area, thus improving the efficacy of the gellant.

The invention thus being described, it will be obvious that the same may be varied in many ways. Such variations are not to be regarded as a departure from the spirit and scope of the invention and all such modifications are intended to be included within the scope of the claims.

What is claimed:
1. An improved organophilic clay gellant useful in providing rheological properties to non-aqueous fluid systems comprising the reaction product of:

(a) one or more smectite clays having a cation exchange capacity of at least 75 milliequivalents per 100 grams of natural clay without impurities;
(b) a first organic cation in an amount of from about 75% to about 150% of the cation exchange capacity of the smectite clay;
(c) a second organic cation provided by a polyalkoxylated quaternary ammonium salt from about 0.01 to 20% by weight of the total amount of organic cations; and
(d) one or more organic anion that is capable of reacting with said first and/or second organic cations to form a complex with said smectite clay.

2. The organophilic clay gellant of claim 1, wherein said smectite clay or clays is selected from the group consisting of montmorillonite, bentonite, hectorite and mixtures thereof.

3. The organophilic clay gellant of claim 1, wherein said first organic cation is provided by a compound selected from the group consisting of quaternary ammonium salts, phosphonium salts, sulfonium ,salts and mixtures thereof.

4. The organophilic clay gellant of claim 1, wherein said first organic cation comprises a hydrophobic organic cation.

5. The organophilic clay gellant of claim 1, wherein said first organic cation is provided by a compound selected from the group consisting of:

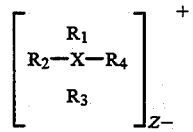

and

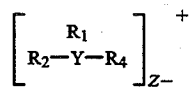

wherein X is nitrogen or phosphorous, Y is sulfur, $R_1$ is a linear or branched, saturated or unsaturated alkyl group having 12 to 22 carbon atoms and $R_2$, $R_3$ and $R_4$ are independently selected from the group consisting of (a) linear or branched alkyl groups having 1 to 22 carbon atoms; (b) aralkyl groups which are benzyl and substituted benzyl moieties including fused ring moieties having linear chains or branches of 1 to 22 carbon atoms in the alkyl portion of the structure; (c) aryl groups such as phenyl and substituted phenyl including fused ring aromatic substituents; (d) beta, gamma unsaturated groups having six or less carbon atoms or hydroxyalkyl groups having 2 to 6 carbon atoms; and (e) hydrogen; and wherein $Z^-$ is an anion.

6. The organophilic clay gellant of claim 1, wherein said second organic cation is provided by a hydrophilic polyalkoxylated quaternary ammonium salt.

7. The organophilic clay gellant of claim 1, wherein said second organic cation is present in an amount of from about 0.01 to about 30 milliequivalents per 100 grams of clay.

8. The organophilic clay gellant of claim 1, wherein said organic anion or anions is provided by a compound selected from the group consisting of carboxylic acids, sulfonic acids, alkyl sulfates and mixtures thereof, either in their form of an acid or in the form of a salt.

9. The organophilic clay gellant of claim 8, wherein said carboxylic acids or their salts are selected from the group consisting of stearic acid, oleic acid, palmitic acid, succinic acid, tartaric acid and mixtures thereof or their salts.

10. The organophilic clay gellant of claim 1, wherein said organic anion or anions has an average molecular weight of about 3000 or less.

11. The organophilic clay gellant of claim 1, wherein said organic anion or anions is provided in an amount sufficient to react with said smectite clay and said first and second organic cations, wherein the milliequivalent ratio of said first and second organic cations to said organic anion or anions is from about 1.70:1.0 to about 50:1.0.

12. A process for preparing an organophilic clay gellant which comprises:
 (a) preparing an aqueous slurry of a smectite clay having a cation exchange capacity of at least 75 milliequivalents per 100 grams of natural clay without impurities:
 (b) heating said slurry to a temperature between about 20° C. and 100° C.;
 (c) adding to said slurry
  (i) a first organic cation in amount of from about 75% to about 150% of the cation exchange capacity of the smectite clay;
  (ii) a second organic cation provided by a polyalkoxylated quaternary ammonium salt from about 0.01 to 20% of the total amount of organic cations;
  (iii) one or more organic anion that is capable of reacting with said first and/or second organic cations:
 (d) reacting the resulting mixture for a sufficient time to form an organophilic clay gellant; and
 (e) recovering said organophilic clay gellant.

13. The process of claim 12, wherein said second cation is provided by a hydrophilic polyalkoxylated quaternary ammonium salt.

14. The process of claim 12, wherein said organic anion or anions is added in an amount sufficient to react with said smectite clay and said first and/or second organic cations, wherein the milliequivalent ratio of said first and second organic cations to said organic anion or anions is from about 1.70:1.0 to about 50:1.0.

15. The process of claim 12, wherein said first and second organic cations and said organic anion are added simultaneously to said aqueous slurry.

16. A non-aqueous fluid system which comprises:
 (a) a non-aqueous composition; and
 (b) an organophilic clay gellant comprising the reaction product of:
  (i) a smectite clay having a specified cation exchange capacity;
  (ii) a first organic cation in an amount of from about 75% to about 150% of the cation exchange capacity of the smectite clay;
  (iii) a second organic cation provided by a polyalkoxylated quaternary ammonium salt from about 0.01 to 20% of the total amount of organic cations; and
  (iv) one or more organic anion that is capable of reacting with said first and/or second cations to form a complex with said smectite clay.

17. The non-aqueous fluid system of claim 16, wherein said non-aqueous composition is selected from the group consisting of paints, coatings, varnishes, enamels, waxes, paint-varnish, lacquer remover, oil base drilling fluids, greases, inks, polyester resins, epoxy resins, mastices, adhesives, sealants, cosmetics and detergents.

18. The non-aqueous fluid system of claim 17, wherein said organophilic clay gellant is present in an amount of about 0.01% to about 15% based on the total weight of said non-aqueous fluid system.

* * * * *